(12) United States Patent
Falco et al.

(10) Patent No.: US 6,622,816 B2
(45) Date of Patent: Sep. 23, 2003

(54) PERSONAL PROTECTIVE DEVICES HAVING AN ENERGY ACTIVATED MATERIAL

(75) Inventors: Robert N. Falco, Indianapolis, IN (US); Cynthia A. Kladden, Indianapolis, IN (US)

(73) Assignee: Cabot Safety Intermediate Corp., Southbridge, MA (US)

( * ) Notice: Subject to any disclaimer, the term of this patent is extended or adjusted under 35 U.S.C. 154(b) by 0 days.

(21) Appl. No.: 09/841,479

(22) Filed: Apr. 24, 2001

(65) Prior Publication Data

US 2002/0153192 A1 Oct. 24, 2002

(51) Int. Cl.[7] .................................................. A61B 7/02
(52) U.S. Cl. ....................... 181/135; 181/126; 181/128; 181/129; 181/130
(58) Field of Search ................................ 181/135, 126, 181/128–130, 134

(56) References Cited

U.S. PATENT DOCUMENTS

| | | | |
|---|---|---|---|
| 4,488,547 A | | 12/1984 | Mason .................. 128/202.22 |
| 4,567,122 A | * | 1/1986 | Baldry et al. .................. 430/4 |
| 4,681,791 A | * | 7/1987 | Shibahashi et al. ........... 428/96 |
| 5,333,622 A | | 8/1994 | Casali .......................... 128/864 |
| 5,480,482 A | | 1/1996 | Novinson .................... 106/498 |
| 5,517,700 A | | 5/1996 | Hoffman ......................... 2/428 |
| 5,591,255 A | | 1/1997 | Small et al. ............. 106/31.61 |
| 5,617,849 A | * | 4/1997 | Springett et al. ...... 128/206.24 |
| 5,811,742 A | | 9/1998 | Leight .......................... 181/135 |
| 5,997,849 A | | 12/1999 | Small et al. .................. 424/61 |
| 6,105,715 A | | 8/2000 | Knauer ....................... 181/135 |
| 6,328,446 B1 | * | 12/2001 | Bhalakia et al. ............. 351/163 |
| 2002/0136899 A1 | * | 9/2002 | deRojas et al. ............. 428/412 |

FOREIGN PATENT DOCUMENTS

GB     2 30 6346     5/1997

OTHER PUBLICATIONS

C.T.I. 4320 Northpark Drive Suite B Colorado Spring, CO 80907–4247 USA.*
Substrates 1997, 1998, 1999, 2000, Chromatic Technologies, Inc.*
Color Option 1997, 1998, 1999, 2000 Chromatic Technologies, Inc.*
Water–Based Flexo Data.*
CTI Chromatic Technologies, Incorpated Dynacolor Data Sheet Thermochromic Water–Based Flexographic Ink.*
Journal of Chemical Education 1999 Division of Chemical Education, Inc. American Chemcal Society.*
Madsci Network: Chemistry Copyright 1996 Washington,.*
Thermochromic Colorant Serials.*
"International Search Report", PCT/US02/11680, Aug. 5, 2002.

* cited by examiner

*Primary Examiner*—Shih-Yung Hsieh
(74) *Attorney, Agent, or Firm*—Cantor Colburn LLP (57) ABSTRACT

A personal protective device is disclosed. The personal protective device comprises at least one energy-activated material, disposed within or on the personal protective device. The energy activated material changes reversibly changes at least a portion of the personal protective device from a first visual zone to a second visual zone when the personal protective device is exposed to an activation energy. An earplug, a pair of earmuffs, a respirator, and eyewear are also disclosed. A method for determining the fit of a personal protective device is also disclosed.

37 Claims, 4 Drawing Sheets

PERSONAL PROTECTIVE DEVICES HAVING AN ENERGY ACTIVATED MATERIAL

BACKGROUND

Personal protective equipment is needed to protect workers in industrial and other work environments, as well as protecting individuals in recreational environments. Typical personal safety protective products include conventional earplugs, earmuffs, respirators, eyewear, and the like, which function to reduce the negative effects of an individual's exposure to debris, dangerous contaminants, or high noise frequencies.

Many work environments require the use of protective equipment under corporate or other policies for safety reasons. In many cases, the workers do not properly wear the protective equipment. For example, with earplugs, to the casual observer, it appears that these individuals are in compliance with the existing safety rules, when in fact the earplugs are not properly inserted. The wearer is generally not aware that the earplug is not properly inserted and the consequences of improper insertion are that the wearer is exposed to greater levels of noise and greater risks. Even a trained individual, such as a supervisor or health and safety officer, may mistakenly believe that the individual is complying with the existing rules based solely on visual observance. Unless the trained individual closely observes the manner in which the protective equipment is put on the individual, it is difficult to judge whether any individual is in full compliance with existing safety rules.

Accordingly, it has been found to be very difficult to enforce the use of the protective equipment without having spot checks. When an individual is subjected to a spot check, the individual must discontinue working and thus productivity is lost due to the spot check. As the number of spot checks and the number of persons subjected to them increases, productivity will continue to decrease resulting in lower profitability and increasing production times.

SUMMARY

The above-discussed and other drawbacks and deficiencies of the prior art are overcome or alleviated by the personal protective devices having an energy-activated material.

A personal protective device is disclosed. The personal protective device comprises at least one energy-activated material, disposed within or on the personal protective device. The energy-activated material reversibly changes at least a portion of the personal protective device from a first visual zone to a second visual zone when the personal protective device is exposed to an activation energy.

An earplug is disclosed. The earplug comprises at least one energy-activated material, disposed within or on the earplug. The energy-activated material reversibly changes at least a portion of the earplug from a first visual zone to a second visual zone when the earplug is exposed to an activation energy.

A pair of earmuffs is disclosed. The pair of earmuffs comprises at least one earmuff. At least one energy-activated material is disposed within or on at least one cushion of the earmuff. The energy-activated material reversibly changes at least a portion of the cushion from a first visual zone to a second visual zone when the cushion is exposed to an activation energy.

A respirator is disclosed. The respirator comprises a respirator having a mask. At least one energy-activated material is disposed within or on the mask. The energy-activated material reversibly changes at least a portion of the mask from a first visual zone to a second visual zone when the mask is exposed to an activation energy.

A pair of eyewear is disclosed. The pair of eyewear comprises at least one energy-activated material, disposed within or on at least one cushion of the eyewear. The energy-activated material reversibly changes at least a portion of the cushion from a first visual zone to a second visual zone when the cushion is exposed to an activation energy.

A method for determining the fit of a personal protective device is disclosed. The method comprises fitting a personal protective device on a wearer. The personal protective device has an energy-activated material on or within the personal protective device. The fit is determined when the energy-activated material reversibly changes from a first visual zone to a second visual zone when the personal protective device is exposed to an activation energy.

The above-discussed and other features and advantages will be appreciated and understood by those skilled in the art from the following detailed description and drawings.

BRIEF DESCRIPTION OF THE DRAWINGS

Referring now to the drawings, wherein like elements are numbered alike in the several figures.

DETAILED DESCRIPTION

Personal protective equipment generally relies on the wearer establishing a proper fit to ensure the protection of the wearer. However, because not every person has the same dimensions, achieving a proper fit can be difficult. A means for demonstrating that a proper fit has been achieved can be determined by a change in appearance (e.g., color or design), at the point where the equipment interacts with the wearer. This personal protective equipment can include earplugs, ear muffs, respirators, eyewear, nose plugs, and the like. Additionally, the use of personal protective equipment that produces a change in appearance (e.g., color or design) can also be aesthetically pleasing promoting the use of the personal protective equipment.

Figure 1A:
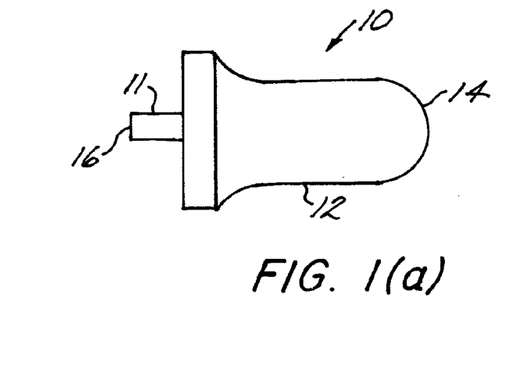
FIG. 1(a) is a perspective view of an exemplary earplug.
Figure 2A:
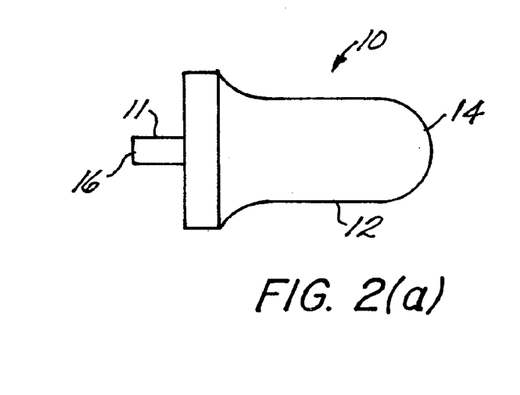
FIG. 2(a) is a perspective view of an exemplary earplug.

Referring now to FIGS. 1(a) and 2(a) in which an exemplary earplug construction according to a first embodiment of the present invention is illustrated and generally indicated at 10. Although the earplug illustrated in FIGS. 1(a) and 2(a) is a mushroom-shaped earplug, other earplugs are contemplated, including cone-shaped, bullet-shaped, multi-flange-shaped, and the like, or any other earplugs which are, or which may become, known to those skilled in the art. Examples of suitable earplug types, shapes, and materials are described in U.S. Pat. Nos. 4,193,396, 4,461,290, 4,936,411, 5,188,123, 5,203,352, 5,792,998, 5,799,658, 5,811,742, 5,904,143, 5,988,313, and U.S. Pat. No. 6,129,175, all of the contents of which are incorporated herein by reference.

The earplug 10 comprises a stem 11 and body 12. The earplug 10 is generally mushroom-shaped and has an insertion end 14 and an opposing second end 16. The diameter of the body 12 of the earplug 10 is somewhat greater than that of the average adult human ear canal.

Figure 1B:
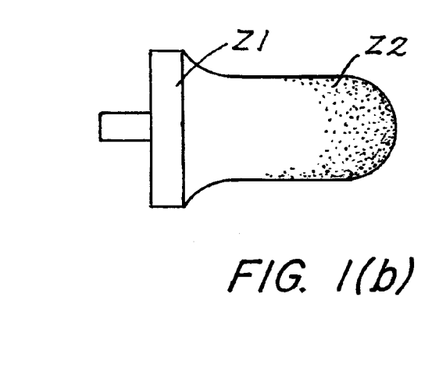
FIG. 1(b) is a view of an exemplary earplug when initially exposed to activation energy.
Figure 1C:
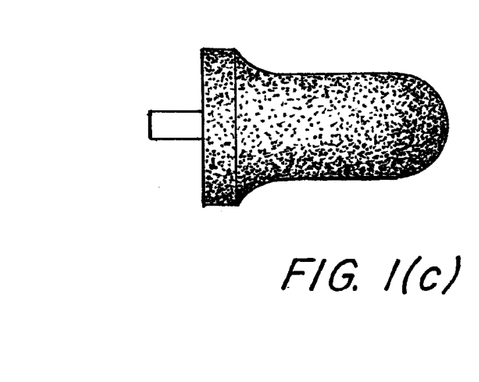
FIG. 1(c) is a view of an exemplary earplug changing to a second visual zone when exposed to activation energy.
Figure 2B:
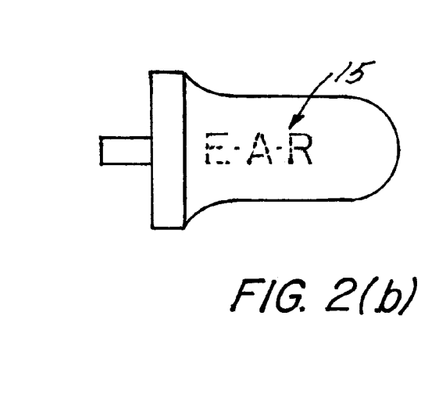
FIG. 2(b) is a view of an exemplary earplug when initially exposed to activation energy.
Figure 2C:
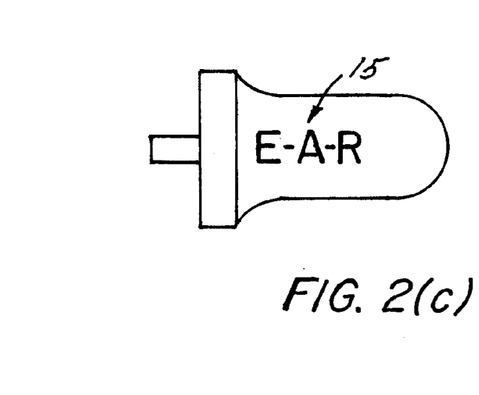
FIG. 2(c) is a view of an exemplary earplug changing to a second visual zone when exposed to activation energy.

The earplugs of the present invention may be formed from any number of suitable materials including foams and non-foams. The earplug can be comprised of a material suitable for creating earplugs, including polyurethane, silicone, polyvinyl chloride foam, plasticized polymeric foams, temperature-dependent viscoelastic polymeric foams, dynamically stiff foams, rubber, polymer gels, thermoplastic elastomers, and combinations comprising at least one of the foregoing materials. In accordance with this invention, included within or on the foregoing earplug material is an energy-activated material present in an amount effective to exhibit a visual change, preferably a color change, upon exposure to an activation energy, preferably thermal energy, as illustrated sequentially in FIGS. 1(a), 1(b), and 1(c) and FIGS. 2(a), 2(b), and 2(c). Thus, for example, when inserting the earplug 10 into a wearer's ears, the earplug interacts with the thermal energy in the interior of the ear canal and changes color (e.g., from vermillion to yellow) creating at least two visual zones. A first zone Z1 is the color of the earplug prior to insertion (e.g., vermillion) (see FIG. 1(a)) and a second visual zone Z2 is the color of the earplug when it is exposed to and is absorbing thermal energy from the interior of the ear canal (e.g., yellow) (see FIG. 1(b)). FIG. 1(c) illustrates the change in color of at least a portion of the earplug 10 when exposed to the activation energy. This change in color (or activation of the energy activated material) preferably occurs when the temperature where the earplug is located is at about 50° F. to about 90° F., with about 70° F. to 80° F. preferred, and with about 75° F. (about 24° C.) especially preferred. The edge of the change in color will spread to at least a portion of the exterior portion of the earplug, or the entire earplug, enough to be visually apparent to an observer that a proper fit has been achieved for maximum attentuation. The color change can also include the gradual change in intensity of the color (i.e., shading). (See FIG. 1(b) and FIG. 1(c)) For example, a white earplug may slowly change in appearance revealing a light red color when exposed to the activation energy prior to changing to a red color of higher intensity when it reaches the appropriate temperature. This change, when exposed to the activation energy, is also illustrated sequentially in FIGS. 2(a), 2(b), and 2(c) with the appearance of a design (or pattern or logo) 15. This appearance of the design 15 can also include the gradual change in the intensity of the appearance of the design 15. (See FIG. 2(b) and FIG. 2(c)).

Another example includes a change in appearance (e.g., color or design) when there is an absence or a presence of light. In this case, the energy-activated material of the earplug 10 is a photochromic pigment. Upon insertion of the earplug 10 into the ear canal, the earplug 10 interacts with the lack of an activation energy (e.g., radiant energy or light) in the interior of the ear canal and changes color (e.g., from vermillion to yellow) creating at least two visual zones. The first zone Z1 is the color (e.g., vermillion) of the earplug prior to insertion and the second visual zone Z2 is the color (e.g., yellow) of the earplug when it is no longer exposed to an activation energy (e.g., radiant energy). The edge of the change in color will spread to at least a portion of the exterior portion of the earplug, or the entire earplug, enough to be visually apparent to an observer that a proper fit has been achieved for maximum attentuation. The color change can also include the gradual change in intensity of the color (i.e., shading). For example, a white earplug may slowly change in appearance revealing a light red color when exposed to the activation energy prior to changing to a red color of higher intensity. The appearance of the design can also include the gradual change in the intensity of the appearance of the design when exposed to the activation energy. The change in appearance (e.g., color, design, etc.) in accordance with this invention is achieved by adding an effective amount of energy-activated material, such as thermochromic and/or photochromic color pigment or dye to the earplug composition, either prior to forming or after forming the earplug, which can aid in determining or achieving a proper fit. Appropriate thermochromic and photochromic pigments are available under the trade name of Chromicolor® and Photopia®, respectively, from Matsui Shikiso Chemical Co. The energy-activated material can be dispersed throughout the earplug material (e.g., foam or other appropriate earplug material) or provided as a coating (or layer) to the surface of the earplug. When disposing the energy activated material on the surface of the earplug, the energy-activated material can be patterned or evenly distributed.

The amount of the energy-activated material utilized should be sufficient to produce the change in appearance (e.g., color or design) and is dependent upon whether the energy activated material is added prior to, or after, the forming the earplug. As an alternative to a change in color and design, a symbol, or a pattern (i.e., a heart, a logo, etc.) can be utilized.

For example, any amount of the color visible or a change in the color of the design or the appearance of a design, could indicate visually to an observer that a proper fit between the earplug 10 and the ear canal has been achieved. If the change is not visually apparent, the earplug 10 should be removed and re-fitted. This lack of color change also indicates that the wearer is only experiencing a low level of sound attenuation because the earplug 10 is not properly inserted into the ear. It is to be understood that the change in color is not limited to the use of vermillion and yellow, any number of color combinations may be used so long as the colors change in a manner which permits the observer to readily and easily know a proper fit is achieved between the earplug 10 and the ear canal.

Furthermore, the use of change in appearance helps to aid the wearer in obtaining a better fit for the earplug 10. For example instead of the safety officer being the observer, the wearer may view the depth of insertion of the earplug 10 into the wearer's ear by using appropriate devices, e.g., a mirror. By observing the appearance change that is visible, the wearer can immediately ascertain the degree of the fit and the corresponding level of sound attenuation being offered by the earplug 10. Adjustments may then be made, if needed, so that the earplug 10 is properly being worn.

Although the change in color, or appearance of a design, symbol or pattern, can indicate a proper fit, the reversible change is also aesthetically pleasing. Accordingly, a variety of colors, designs, or logos can be utilized on the earplug 10 for aesthetic reasons in an effort to promote use of the earplug.

Figure 3:
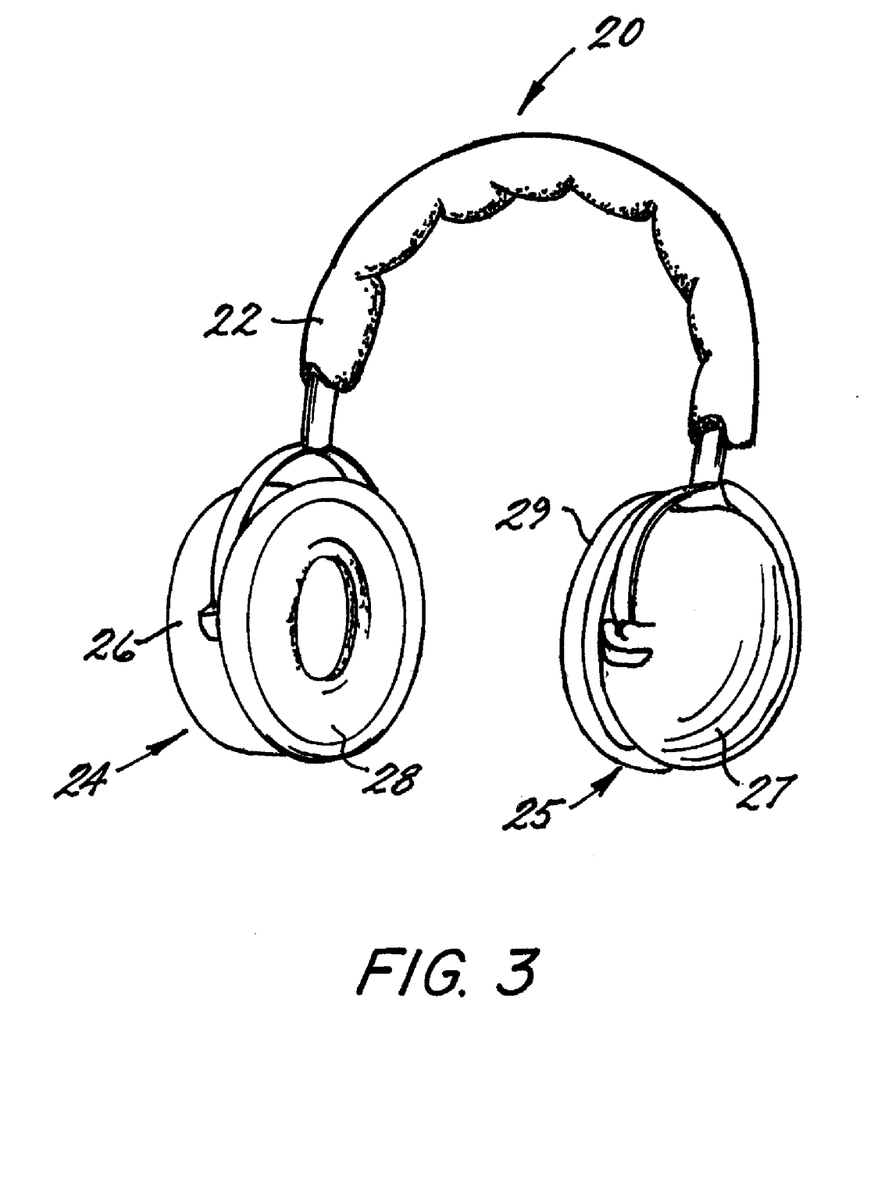
FIG. 3 is a perspective view of an exemplary earmuff.

Referring now to FIG. 3, an exemplary earmuff construction according to a second embodiment of the present invention is illustrated and generally indicated at 20. The earmuff 20 is comprised of a connecting member and a pair of muffs suitable for covering the wearer's ears. The muffs are suspended from opposite portions of the connecting member. Although the connecting member illustrated in FIG. 3 is a headband 22, other members are contemplated, including a helmet with auxiliary hardware or any other means which are, or which may become, known to those skilled in the art. Examples of suitable ear muff types, shapes, and materials are described in U.S. Pat. Nos. 4,459,707, 5,924,138, 5,970,160, 5,979,451, 6,148,446, all of the contents of which are incorporated herein by reference.

The earmuff 20 comprises a headband 22 and muffs 24, 25. Muffs 24, 25 are comprised of cups 26, 27 and ear seal cushions 28, 29. The cups 26, 27 and/or the ear seal cushions 28, 29 can be at least partially or entirely porous. The ear seal cushions 28, 29 can be comprised of a material including polyurethane, silicone, polyvinyl chloride foam, plasticized polymeric foams, temperature-dependent viscoelastic polymeric foams, dynamically stiff foams, rubber, polymer gels, thermoplastic elastomers, and the like, and combinations comprising at least one of the foregoing materials. The ear seal cushions 28, 29 can be coated with a nonporous material such as vinyl, polyurethane, silicone, and the like, as well as combinations comprising at least one of the foregoing materials.

The material of the ear seal cushions 28, 29 or the material chosen to coat the ear seal cushions 28, 29 can be combined with the energy-activated material described above (e.g., thermochromic pigments, photochromic pigments, etc.). The energy-activated material can be dispersed throughout the ear cushion foam (or other appropriate ear cushion material) or provided as a coating (or layer) to the surface of the ear cushion. When disposing the energy-activated material on the surface of the ear cushion, the energy-activated material can be patterned or evenly distributed. The amount of the energy-activated material utilized should be sufficient to produce the change in apperance (e.g., color or design) and is dependent upon whether the energy-activated material is added prior to, or after, the forming the ear cushion.

An example of using the earmuff is as follows. When the wearer places the earmuff 20 over his/her ears, any amount of the appearance change (e.g., color or design) visually apparent to an observer can indicate that a proper fit is achieved. If an appearance change does not appear in the proper places, then there is a poor fit and consequently, the earmuff 20 should be removed and re-fitted. This also indicates that the wearer is only experiencing a low level of sound attenuation because the earmuff 20 is not properly inserted onto the ear. Accordingly, the appearance change (e.g., color or design) is visually apparent and permits a safety officer, the wearer, or other individual to ascertain whether the wearer is complying with existing safety rules and regulations.

Although the change in appearance (e.g., color or design) can indicate a proper fit, the reversible change is also aesthetically pleasing and so can promote use of the earmuff. A variety of colors, designs, or logos can be utilized on the earmuffs 20.

Figure 4:
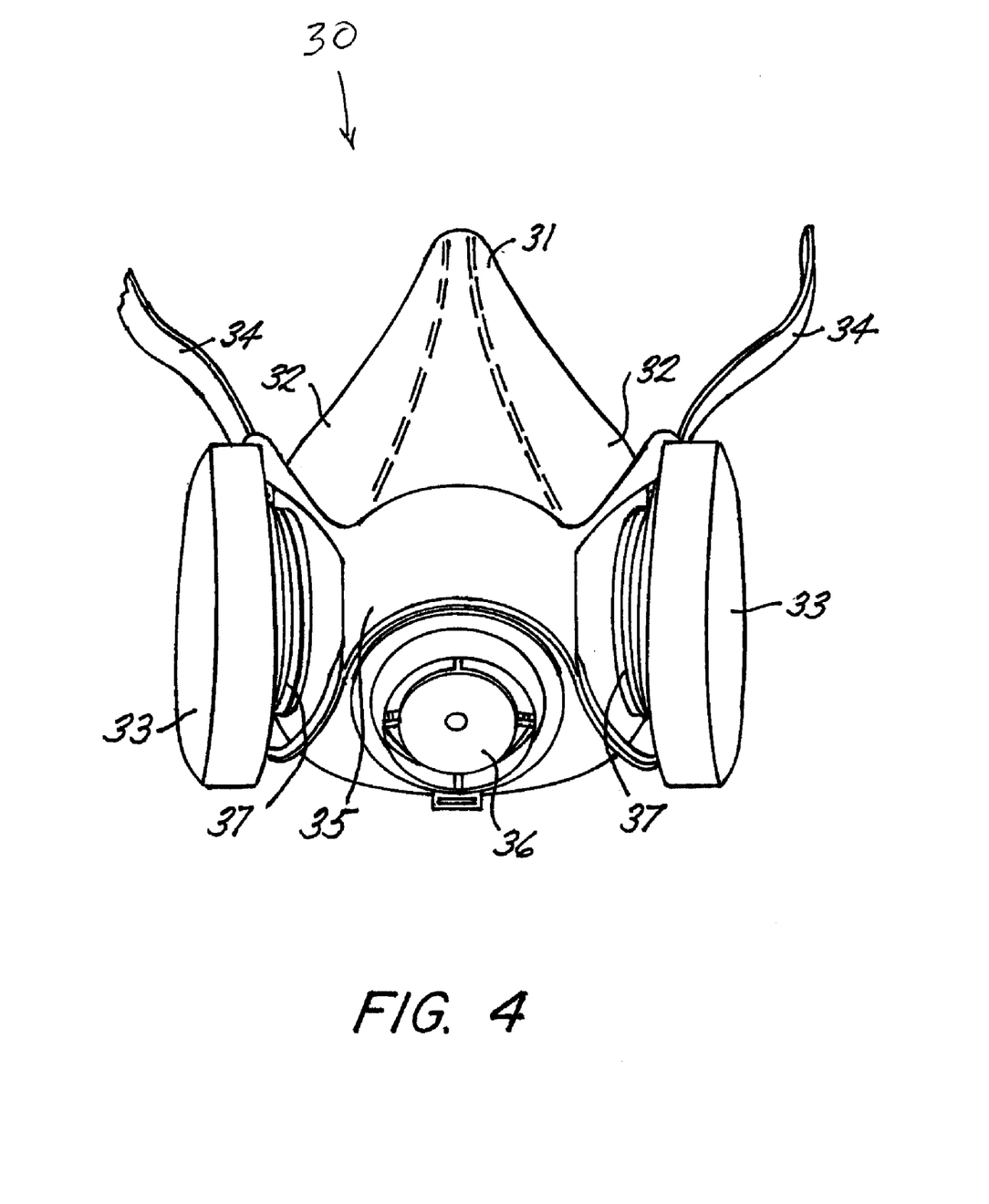
FIG. 4 is a perspective view of an exemplary respirator.

Referring now to FIG. 4, an exemplary respirator construction according to a third embodiment of the present invention is illustrated and generally indicated at 30. Although a half-mask respirator is illustrated, use with a full-face respirator, a face mask, and the like is also contemplated, or any other means which are, or which may become, known to those skilled in the art. Examples of suitable respirator types, shapes, and materials are described in U.S. Pat. Nos. 4,454,881, 4,592,350, 4,600,002, 5,924,420, 6,116,236, all of the contents of which are incorporated herein by reference.

The respirator 30 comprises a mask 31 with inclined side walls 32 which flare from an apex and is intended to fit over the bridge of the nose of the user to flattened side surfaces. The mask 31 has an in-turned flexible sealing lip or flange having a radius, which extends around the entire edge that is intended to come into contact with the face of the user. This flange is contoured generally to conform to and form a leak-free seal with the user's face.

Chemical cartridges 33 are shown as being attached to the upstream side of inhalation valve housings (or fittings) 37 in which are mounted flexible disk-type inhalation valves (not shown). An exhalation fitting 36, having an exhalation valve, is located at the base of the mask 31. The halter (or yoke) 35 is formed of a material having sufficient flexibility and resilience to readily conform to the contour of the mask 31 is provided with structural ring portions that fit around the inhalation valve housings 37 in the side wall portions in the mask 31. The yoke 35 also has fastening means for the attachment of suspension straps 34 to connect the mask 31 to a headpiece (not shown).

The material of the mask 31 has sufficient inherent flexibility and its thickness is selected so that it readily conforms to the facial structure of a wide range of potential users. Suitable mask 31 materials include polyurethane, silicone, polyvinyl chloride foam, plasticized polymeric foams, temperature-dependent viscoelastic polymeric foams, dynamically stiff foams, rubber, polymer gels, thermoplastic elastomers, and the like, as well as combinations comprising at least one of the foregoing materials.

The material of the mask 31 (and/or any associated sealing lip or flange) can be combined with the energy-activated material described above (e.g., thermochromic pigments, photochromic pigments, etc.). The energy-activated material can be dispersed throughout the rubber (or other appropriate mask material) or provided as a coating (or layer) to the surface of the mask. When disposing the energy-activated material on the surface of the mask, the energy-activated material can be patterned or evenly distributed. The amount of the energy-activated material utilized should be sufficient to produce the change in appearance (e.g., color or design) and is dependent upon whether the energy-activated material is added prior to, or after, the forming the mask.

An example of using the respirator is as follows. A wearer typically puts on (dons) a respirator by clipping the lower straps behind the neck and then lifting the headpiece (or cradle) up onto the top of the crown while simultaneously guiding the face mask and yoke portion into position on the face. The straps are then manipulated and adjusted until a good fit is achieved and a successful face seal check is performed. Removal, or doffing, of the respirator is performed opposite the donning operation wherein the lower straps are unbuckled and the cradle is removed from the head while the face mask is withdrawn from the face of the wearer. In the course of an average day a worker required to wear a respirator may don and doff the respirator up to 20 times.

The appearance change (e.g., color or design) is visually apparent to permit a safety officer, the wearer, or other individual to ascertain whether the wearer is complying with existing safety rules and regulations. For example, when the wearer fits the respirator 30 to his/her face any amount of the appearnce change (e.g., color or design) visually apparent to an observer will indicate that a proper fit is achieved. If a appearance change does not appear in the proper places, then there is a poor fit and consequently, the respirator 30 should be removed and re-fitted. This also indicates that the wearer is not protected against breathing in potentially harmful contaminants since the respirator 30 is not properly fitted to the face.

Although the change in appearance (e.g., color or design) can indicate a proper fit, the reversible change is also aesthetically pleasing and so can promote use of the respirator. A variety of colors, designs, or logos can be utilized on the respirator 30.

Figure 5:
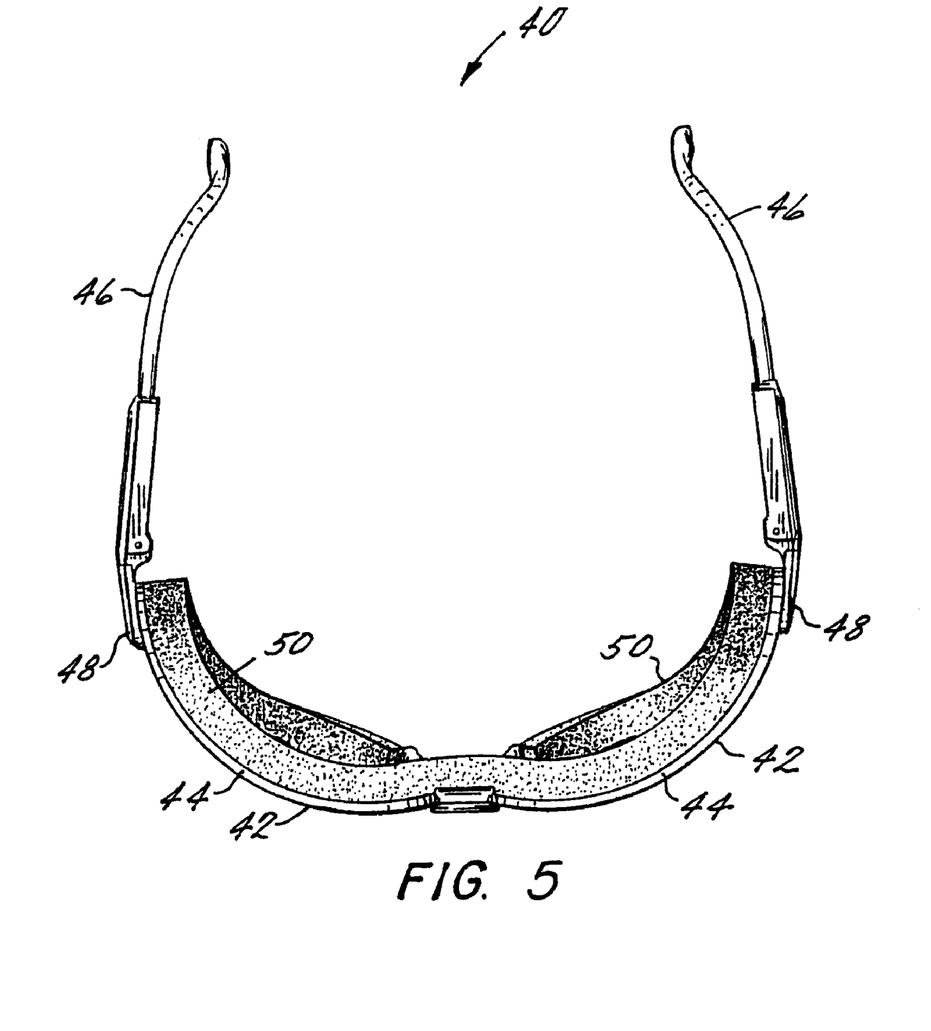
FIG. 5 is a perspective view of an exemplary eyewear.

Referring now to FIG. 5, an exemplary pair of eyewear according to another embodiment of the present invention is illustrated and generally indicated at 40. In particular, plano eyewear for use in safety and recreational (i.e., sports) applications is contemplated (although this invention would be equally suitable for eyewear incorporating prescription lenses). Examples of suitable eyewear applications include spectacles, goggles, face shields, respirator lenses, visors, helmets and the like. Examples of suitable eyewear types, shapes, and materials are described in U.S. Pat. Nos. 5,138,723, 5,345,616, 5,617,588, 5,983,390, all of the contents of which are incorporated herein by reference. Although a pair of safety goggles are illustrated, the invention is not limited and includes all eyewear utilized as protective equipment or any other eyewear which are, or which may become, known to those skilled in the art.

The eyewear 40 comprises lenses 42 which are connected to rims 44. Temple bodies 46 attach to the rims 44 at attachment points 48. Disposed along the rim towards the interior of the eyewear 40 is a cushion material 50. The cushion material 50 provides for a seal against the wearer's face to prevent the splashing or intrusion of contaminants into the wearer's eyes.

The material of the cushion 50 has sufficient inherent flexibility and its thickness is selected so that it readily conforms to the facial structure of a wide range of potential users. Suitable materials for the cushion 50 include polyurethane, silicone, polyvinyl chloride foam, plasticized polymeric foams, temperature-dependent viscoelastic polymeric foams, dynamically stiff foams, rubber, polymer gels, thermoplastic elastomers, and the like, as well as combinations comprising at least one of the foregoing materials.

The material of the cushion 50 can be combined with the energy-activated material described above (e.g., thermochromic pigments, photochromic pigments, etc.). The energy-activated material can be dispersed throughout the cushion 50 material (e.g., foam or other appropriate cushion material) or provided as a coating (or layer) to the surface of the cushion 50. When disposing the energy-activated material on the surface of the cushion 50, the energy-activated material can be patterned or evenly distributed. The amount of the energy-activated material utilized should be sufficient to produce the change in appearance (e.g., color or design) and is dependent upon whether the energy-activated material is added prior to, or after, the forming the cushion 50.

The appearance change (e.g., color or design) is visually apparent to permit a safety officer, the wearer, or other individual to ascertain whether the wearer is complying with existing safety rules and regulations. An example of using the eyewear 40 is as follows. When the wearer fits the eyewear 40 to his/her face any amount of the appearance change (e.g., color or design) visually apparent to an observer will indicate that a proper fit is achieved. If an appearance change does not appear in the proper places, then there is a poor fit and consequently, the eyewear 40 should be removed and re-fitted. This also indicates that the wearer is not protected against splashing of contaminants because the eyewear 40 is not properly fitted to the face.

The personal safety protective products having an energy activated material is not limited to the color configurations or designs recited hereinbefore and any number of color schemes and designs may be used so long as the visual zones are visually distinct from each other. For example, the visual zones include the color zone when not exposed to the temperatures of the human body (i.e., vermillion) and the color zone exposed to the temperature of the human body (i.e., yellow). Accordingly, the visual zones permit an observer or the wearer to immediately ascertain the degree of fit by simply viewing which visual zone(s) is visible. This permits a safety officer or other individual, including the wearer, to easily determine whether the wearer is complying with existing safety rules and regulations.

The use of colors is not limited to the use of vermillion or yellow and a number of color combinations may be used so long as the colors mark or indicate the change in temperature, which permit the observer to readily and easily know the type of fit. For example, instead of the safety officer being the observer, the wearer may view the proper fit of the protective equipment by using appropriate devices, e.g., a mirror. By observing the visible change of color, the wearer can immediately ascertain the degree of the fit and the corresponding level of protection being offered by the device. Adjustments may then be made, if needed, so that the device is properly being worn.

Accordingly, the personal safety protective products with proper fit characteristics provides an effective visual aid in determining whether the wearer is complying with existing safety rules, regulations, and the like and also provides a visual aid to permit the wearer to obtain a better fit. By observing which visual zones change appearance (e.g., color or reveals a pattern or design) and which visual zone is not altered, an observer or the wearer himself/herself may easily determine the proper fit. Advantageously, this permits the wearer to be easily instructed as to the proper fit that is required in any given environment by simply referencing the visual zones of the device and indicating which visual zones may or may not be visible during use of the device. In addition, the multicolored device or device with logos, patterns or symbols, are visually pleasing and appealing; and as a result, the incorporation of this invention in personal protective equipment may aid in user acceptance in the workplace.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A personal protection device to be worn by a wearer, the device comprising:

a body;

an energy activated material disposed in or on said body; and a visual zone disposed on the body and visible when the device is worn by the wearer;

wherein the energy activated material changes a visual appearance of the visual zone when the energy activated material is exposed to an activation energy, the change in the visual appearance of the visual zone providing an indication of a fit of the device on the wearer while the device is worn by the wearer.

2. The personal protective device of claim 1, wherein the energy activated material comprises a thermochromic material and wherein the activation energy comprises a body heat of the wearer.

3. The personal protective device of claim 1, wherein the energy activated material comprises a photochromic material and wherein the activation energy comprises the presence or absence of light.

4. The personal protective device of claim 1, wherein the change in the visual appearance of the visual zone comprises a change in a color of the visual zone.

5. The personal protective device of claim 4, wherein the change in the color of the visual zone comprises a red color changing to a yellow color.

6. The personal protective device of claim 4, wherein the change in the color of the visual zone comprises a change in an intensity of the color of the visual zone.

7. The personal protective device of claim 1, wherein the change in the visual appearance of the visual comprises an appearance of a design at the visual zone.

8. The personal protective device of claim 7, wherein the appearance of the design comprises a change in a visual intensity of the design.

9. The personal protective device of claim 7, wherein the design comprises at least one of an ornamental pattern, an indicia, and a logo.

10. The personal protective device of claim 1, wherein the indicated fit comprises a proper fit of the device on the wearer such that a desired protection of the wearer is achieved.

11. The personal protective device of claim 10, wherein the desired protection comprises at least one of an ear protection, an eye protection, and a breathing protection.

12. The personal protective device of claim 1, wherein the energy activated material is dispersed throughout the body or comprises a coating applied to a surface of the body.

13. The personal protective device of claim 1, wherein the body comprises an earplug insertable into an ear canal of the wearer.

14. The personal protective device of claim 13, wherein the earplug comprises at least one of a polyurethane, a silicone, a polyvinyl chloride foam, a plasticized polymeric foam, a temperature-dependent viscoelastic polymeric foam, a dynamically stiff foam, a rubber, a polymer gel, and a thermoplastic elastomer.

15. The personal protective device of claim 13, wherein the earplug comprises a substantially cylindrical foam body portion and a semi-rigid stem disposed in the foam body portion.

16. The personal protective device of claim 13, wherein the visual zone is disposed at an external portion of the earplug, the external portion being visible when the earplug is inserted in the ear canal of the user, and wherein the change in the visual appearance comprises at least one of a change in a color of the visual zone and an appearance of a design at the visual zone.

17. The personal protective device of claim 13, wherein the energy activated material comprises a thermochromic material and the activation energy comprises a body heat of the wearer.

18. The personal proactive device of claim 17, wherein the body heat comprises a temperature of about 50° F. to 90° F.

19. The personal protective device of claim 17, wherein the body heat comprises a temperature of about 75° F.

20. The personal protective device of claim 1, wherein the body comprises an earmuff assembly to be worn over ears of the wearer.

21. The personal protective device of claim 20, wherein the earmuff assembly comprises two cups, a headband connecting the two cups, and two ear seal cushions disposed on each of the respective cups.

22. The personal protective device of claim 21, wherein the energy activated material is disposed in the ear seal cushions or comprises a coating applied to the ear seal cushions.

23. The personal protective device of claim 21, wherein the visual zone is disposed on the ear seal cushions and wherein the change in the visual appearance comprises at least one of a change in a color of the visual zone and an appearance of a design at the visual zone.

24. The personal protective device of claim 1, wherein the body comprises a respirator to be worn on a face of the wearer.

25. The personal protective device of claim 24, wherein the respirator comprises a mask which contacts the face of the wearer when the device is worn, the visual zone being disposed on the mask.

26. The personal protective device of claim 25, wherein the energy activated material is disposed in the mask or wherein the energy activated material comprises a coating applied to the mask.

27. The personal protective device of claim 25, wherein the change in the visual appearance comprises at least one of a change in a color of the visual zone and an appearance of a design at the visual zone.

28. The personal protective device of claim 1, wherein the body comprises an eyewear to be worn over eyes of the wearer.

29. The personal protective device of claim 28, wherein the eyewear comprises a lens, a rim connected to the lens, and a cushion material which contacts a face of the wearer when the device is worn.

30. The personal protective device of claim 29, wherein the cushion material comprises at least one of a polyurethane, a silicone, a polyvinyl chloride foam, a plasticized polymeric foam, a temperature-dependent viscoelastic polymeric foam, a dynamically stiff foam, a rubber, a polymer gel, and a thermoplastic elastomer.

31. The personal protective device of claim 29, wherein the visual zone is disposed on the cushion material, and wherein the change in the visual appearance comprises at least one of a change in a color of the visual zone and an appearance of a design at the visual zone.

32. The personal protective device of claim 28, wherein the eyewear is a piano eyewear comprising a lens and a cushion material, the cushion material contacting a face of the wearer when the device is worn, the cushion material including the energy activated material, and the visual zone being disposed on the cushion material.

33. A personal protection device to be worn by a wearer, the device comprising:

a body; and an energy activated material disposed in or on said body;

wherein the energy activated material changes a visual appearance of the body when the energy activated material is exposed to an activation energy, the change in visual appearance providing an indication of a fit of the device on the wearer while the device is worn by the wearer.

34. The personal protective device of claim 33, wherein the body is selected from the group consisting of an earplug, an earmuff, a respirator, and an eyewear.

35. The personal protective device of claim 34, wherein the change in the visual appearance of the body comprises at least one of a change in a color of the body and an appearance of a design on the body.

36. A method of determining a fit of a personal protective device on a wearer, while the device is being worn by the wearer, the method comprising:

observing a visual zone of the device, the visual zone comprising an area of the device visible while the device is worn by the wearer;

noting a change in appearance of the visual zone, while the device is worn by the wearer; and determining the fit of the device on the wearer according to the change in the appearance of the visual zone.

37. A method of disposing a personal protective device on a wearer, the method comprising:

fitting the device on the wearer;

observing a visual zone of the device, the visual zone comprising an area of the device visible while the device is worn by the wearer;

noting a change in appearance of the visual zone, while the device is worn by the wearer;

determining a fit of the device on the wearer according to the change in the appearance of the visual zone; and adjusting the fit of the device according to the change in the appearance of the visual zone.

* * * * *

UNITED STATES PATENT AND TRADEMARK OFFICE
CERTIFICATE OF CORRECTION

PATENT NO.        : 6,622,816 B2                                           Page 1 of 1
APPLICATION NO. : 09/841479
DATED             : September 23, 2003
INVENTOR(S)       : Robert N. Falco et al.

It is certified that error appears in the above-identified patent and that said Letters Patent is hereby corrected as shown below:

<u>Column 10:</u>
Line 1, after "personal", delete "proactive" and insert therefor --protective--;
Line 56, before "eyewear", delete "piano" and insert therefor --plano--.

Signed and Sealed this

Twenty-first Day of August, 2007

JON W. DUDAS
*Director of the United States Patent and Trademark Office*